(12) United States Patent
Karpati

(10) Patent No.: US 8,118,028 B2
(45) Date of Patent: Feb. 21, 2012

(54) INTRAUTERINE CONTRACEPTIVE DEVICE

(76) Inventor: Melinda-Kinga Karpati, Zug (CH)

( * ) Notice: Subject to any disclaimer, the term of this patent is extended or adjusted under 35 U.S.C. 154(b) by 295 days.

(21) Appl. No.: 12/311,152

(22) PCT Filed: Sep. 20, 2007

(86) PCT No.: PCT/EP2007/008202
§ 371 (c)(1),
(2), (4) Date: May 20, 2009

(87) PCT Pub. No.: WO2008/034619
PCT Pub. Date: Mar. 27, 2008

(65) Prior Publication Data
US 2009/0311306 A1    Dec. 17, 2009

(30) Foreign Application Priority Data
Sep. 20, 2006  (EP) .................................... 06019697

(51) Int. Cl.
*A61F 6/06* (2006.01)
*A01N 59/20* (2006.01)
*A01N 59/16* (2006.01)

(52) U.S. Cl. ........ 128/830; 128/832; 128/833; 424/630; 424/641

(58) Field of Classification Search .................. None
See application file for complete search history.

(56) References Cited

U.S. PATENT DOCUMENTS

| | | | |
|---|---|---|---|
| 3,559,641 A * | 2/1971 | Lay | 128/839 |
| 3,563,235 A * | 2/1971 | Zipper | 128/833 |
| 3,711,035 A | 1/1973 | Tatum et al. | |
| 4,026,281 A * | 5/1977 | Mayberry et al. | 128/840 |
| 4,034,749 A * | 7/1977 | Von Kesseru et al. | 128/833 |
| 4,198,966 A | 4/1980 | Kaivola | |
| 4,326,511 A * | 4/1982 | Zimerman | 128/833 |
| 4,353,363 A | 10/1982 | Quesada | |
| 4,562,835 A | 1/1986 | Anderson | |
| 4,658,810 A * | 4/1987 | Bauer | 128/839 |
| 6,322,588 B1 * | 11/2001 | Ogle et al. | 623/1.46 |

FOREIGN PATENT DOCUMENTS

EP       0350087 A1 *  6/1989

OTHER PUBLICATIONS

International Preliminary Report on Patentability for PCT/EP2007/008202, dated Apr. 2, 2009.
Oberzill, W., "On the „Oligodynamic Effect of Silver and its Use for the Disinfection of Drinking Water and Mineral Water," *Scientia pharmaceutica* 24:171-193 (1956). English Translation of Abstract (3 pages).
Gmünd, S., et al., "Silver Cutlery Bactericidal," *Umschau* 6:192 (1955). English Translation of Abstract (1 page).
European Search Report for Application No. EP 06 01 9697, Date of Completion of Report Feb. 16, 2007.
Medel, M., et al., "Contraceptive Efficacy of Two Different Metals Using a Modified Seven Vector," *Int J Gynaecol Obstet* 14:494-498 (1976).
Pearl, R., "Contraception and Fertility in 2,000 Women," *Human Biology* 4:363-407 (1932).
Feb. 5, 2008, International Search Report, PCT/EP2007/008202.
Feb. 5, 2008, Written Opinion of the International Searching Authority, PCT/EP2007/008202.

* cited by examiner

*Primary Examiner* — Robert A Wax
*Assistant Examiner* — Olga V Tcherkasskaya
(74) *Attorney, Agent, or Firm* — Hamilton, Brook, Smith & Reynolds, P.C.

(57) ABSTRACT

An intrauterine contraceptive device comprising a carrier body (1) and an active metallic alloy (4), characterized in that the active metallic alloy is of the formula $Zn_xCu_yMn_zAu_k$ (I) or $Zn_xCu_yMn_zAg_k$ (II), wherein x+y+z+k=100 weight %, x is in the range from approximately 18 to 30 weight %, z is in the range from approximately 0.5 to 3 weight %, and k is in the range from approximately 3 to 12 weight %, y being the balance.

9 Claims, 1 Drawing Sheet

INTRAUTERINE CONTRACEPTIVE DEVICE

RELATED APPLICATIONS

Figure 1:
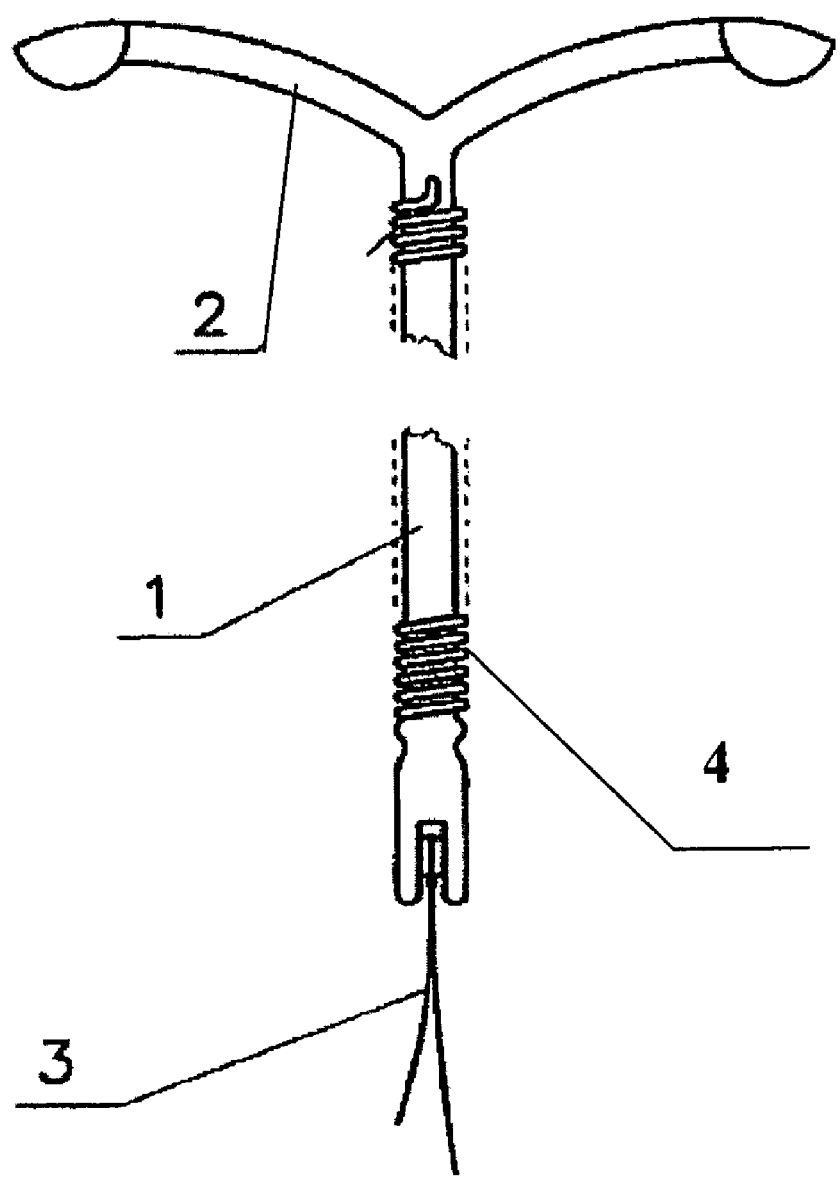

This application is the U.S. National Stage of International Application No. PCT/EP2007/008202, filed Sept. 20, 2007, published in English, and claims priority under 35 U.S.C. §119 or 365 to EP Application No. 06019697.9, filed Sept. 20, 2006.

The present invention relates to an intrauterine contraceptive device (IUD) comprising a carrier body and an active metallic alloy which contains zinc, copper, manganese, gold and/or silver.

The use of intrauterine devices comprising copper as the active metal are known since the seventies. U.S. Pat. Nos. 4,198,966 and 4,353,363 describe intrauterine contraceptive devices comprising a support body equipped with arms on one side and a thread on the opposite side that contain copper as the active ingredient. A wire made of copper is wound in form of a spiral onto the support body. The copper performs a spermicide function on the spermatozoa. It is also known that the use of copper in excess of 200 mm$^2$ is necessary to obtain a reliable contraceptive effectiveness over 3 to 5 years.

U.S. Pat. No. 4,562,835 discloses a T-shaped intrauterine device which carries copper sleeves on its arms and a helical winding of copper wire, also used for contraception.

One known drawback of the intrauterine contraceptive devices of the prior art is that the menstrual blood flow usually increases by 10 to 35 mL and lasts 2 to 4 days longer as usual. Another known drawback is the increasing risk for infections, especially ascending genital infections or infections caused by transmitted bacteria.

It is also known that a combination of zinc and copper as active ingredients increase the contraceptive effectiveness of an intrauterine device. Mendel describes in J. Gynaecol Obstet, 14, 494-498(1976) that a device with 30 mm$^2$ of copper and 47 mm$^2$ of zinc offers a higher contraceptive effectiveness than a device merely contains at least 200 mm$^2$ of copper. Within the device, zinc and copper wires are wound onto the carrier body without the two metals being in contact. The lifetime, however, of such a device, if used in vivo, is reduced to a couple of month due to the occurrence of irregular histological findings after 15 month of use. Thus, the practical applicability of this device could not be set forth. Additionally, Mendel reports that no significant differences in bleeding and pain removal rates were noted between the tested devices.

The object of the present invention is to provide an intrauterine device with an increased contraceptive effectiveness that at the same time induces a shorter and less intensive menstruation compared to intrauterine contraceptive devices known in the art. A further object of the present invention is to provide an intrauterine contraceptive device which reduces the risk for infections in the abdominal region to a minimum.

Both problems are solved by an intrauterine contraceptive device comprising a carrier body and an active metallic alloy, wherein the active metallic alloy is of the formula $$Zn_xCu_yMn_zAu_k \quad (I), or$$

$$Zn_xCu_yMn_zAg_k \quad (II),$$

and wherein x+y+z+k=100 weight %, x is in the range from approximately 18 to 30 weight %, z is in the range from approximately 0.5 to 3 weight %, k is in the range from approximately 3 to 12 weight %, and y being the balance.

Formulas (I) and (II) also comprise alloys where gold and silver are present in combination. Then, the sum of the weight percentages of gold and silver is from approximately 3 to 12 weight %.

In a preferred embodiment of the present invention, the active metallic alloy is wire-shaped. This enables an easy and unproblematic handling of the active metallic alloy, especially within the completion of the intrauterine contraceptive device.

The active metallic alloy can be prepared by any process suitable to form an alloy that comprises at least zinc, copper, manganese, gold or silver or gold and silver. Preferably, the active metallic alloy is prepared by melting and melt-spinning followed by forming a wire and bending it by employing technologies known to a person skilled in the art. Such methods are described, for example within/by Sneed—Maynard—Brasted: Comprehensive Inorganic Chemistry. Copper, Silver and Gold. D., Van Nostrand Comp., Inc., Toronto, New York, London, 1945.

The average diameter of the active metallic alloy wire is in a range from approximately 0.25-0.4 mm, preferably from approximately 0.3-0.4 mm, and most preferably approximately 0.3 mm.

The manganese present in the inventive active metallic alloy is on the one hand necessary to form the alloy comprising a zinc content of 18 weight % or higher and, on the other hand, it is believed to enhance the ameliorating effect over the menstruation.

Due to the presence of manganese, which is an important component of the hormones regulating the functioning of the genitals, and it is also the CO-factor of the vitamin K, which has an important rule in the blood coagulation, the menstruation bleedings are 2 to 4 days shorter and 20 to 60% less intensive during the use of the inventive intrauterine contraceptive device compared to the bleedings caused during the use of intrauterine contraceptive devices comprising merely copper as an active ingredient.

The other effect of manganese is that if no manganese is present during the manufacturing process of an alloy comprising copper, zinc, gold or silver or gold and silver, merely an alloy with the maximum of 17 weight % of zinc can be prepared. An alloy with a zinc content of 17 weight % or lower does not lead to the strived effects of an increasing contraceptive effectiveness and at the same time an induction of a shorter and less intensive menstruation. A minimum of 18 weight % zinc is necessary to reach these effects. In the presence of manganese, the zinc content of the active metallic alloy can be increased up to approximately 30 weight %. On the other hand, the manganese enhances the ameliorating effect over the menstruation.

Without wishing to be restricted to a certain theory, it is believed that the spermicide function of the active ingredient on the spermatozoa and on the menstruation duration can be explained as follows: the copper and zinc within the present active metal alloy act as the contraceptive effective ingredients. When the device is placed in the uterus, the metal alloy comes into contact with the fluids present in the uterus. Consequently, a multitude of galvanic cells will be increased. The anode of theses cells contains the more electronegative compounds of the alloy, copper and zinc, while gold or silver or gold and silver becomes the cathode. Due to the galvanic effect, the metals of the anode are dissolved by forming ions.

As such, copper and zinc develop their contraceptive effectiveness. The cathode, however, remain practically unchanged. The electrochemical dissolution of the metals of the anode according to the present invention, compared to the spontaneous copper dissolution caused within a device merely comprising copper as its active ingredient, is not more intensive. Nevertheless, the presence of copper, zinc, manganese and gold or silver, or gold and silver results in a synergistic effect which, on the one hand, enhances the contraceptive effectiveness and, on the other hand, induces a shorter and less intensive menstruation compared to intrauterine contraceptive devices of the prior art merely equipped with copper as active ingredient.

According to a preferred embodiment of the present invention x+y is approximately 93 weight %, more preferably x is approximately 24 weight % and y is approximately 69 weight %.

The daily release of zinc and copper within the present device is in a range from approximately 48 to 72 µg zinc ions and approximately 200 to 280 µg copper ions. In a preferred embodiment of the present invention the daily release of zinc ions is approximately 60 µg and of copper ions is approximately 240 µg.

Due to the above described properties, the time period in which the inventive intrauterine conceptive device reliably protects from getting pregnant is extended up to 5 years.

Besides the above mentioned synergistic effect, caused by the presence of gold or silver or gold and silver within the inventive device, gold and silver have bactericidal and fungicidal properties. The bactericidal and fungicidal properties of gold and silver are based on their oligodynamical dissolution in traces. The term "oligodynamical dissolution" means that the metal dissolves in traces. For example, in the case of gold and silver, the oligodynamical dissolution is 0.04-1 µg/ml (see: Die oligodynamische Wirkung der Metalle und Metallsalze, Berlin, Springer, 1924; Umschau: 55, 192 (1955); Sci. Pharm. 24, 171 (1956)).

To lower the risk for infections, especially ascending genital infections or infections caused by transmitted bacteria, to a minimum, gold or silver or a combination of gold and silver has to be present in a range from approximately 3-12 weight %, preferably approximately 6 weight %.

According to a further preferred embodiment of the present invention, the composition of the active metallic alloy is as follows:

24 weight % zinc
69 weight % copper
1 weight % manganese
6 weight % gold or silver The contraceptive effectiveness of an intrauterine contraceptive device as described in the above paragraphs is greater than 99.5%, what is equivalent to a Pearl index of 0.5. The Pearl index R is an accepted measure of contraceptive effectiveness. It represents the pregnancy rate per 100 woman-years of use, computed according to Pearl's formula, R=P× 1200/M, in which the numerator is the number of accidental pregnancies multiplied by 1200, and the denominator is the aggregate of all months of exposure contributed by all couples included in the investigation (see Pearl R., Contraception and fertility in 2,000 women, Human Biology 1932, 4: 363-407).

The carrier body of the present device is equipped with arms on one side and an indicator thread on the opposite side of the body. According to the present invention, the active metallic alloy is arranged around a portion of the carrier body placed between the arms and the indicator thread.

In a preferred embodiment, the active metal alloy is wire-shaped and placed onto the carrier body in a helical form. This has the advantage that the release of copper and zinc ions occurs in a steady and uniform way. The helical form is easy to carry out, provides the biggest surface to the alloy and, furthermore, in this case it contains gaps for trapping spermatozoa.

The carrier body of the inventive intrauterine contraceptive device is made of plastic, preferably plastic with flexible properties. The plastic is selected from a group consisting of polyethylene and polypropylene.

In a preferred embodiment the carrier body is made of polyethylene. Polyethylene has the advantage to be inert against the fluids present in the uterus. Additionally, a body made of polyethylene provides sufficient flexibility to be used as a carrier body within an intrauterine contraceptive device as it is claimed herein.

The indicator thread of the present intrauterine contraceptive device can be of any suitable material in the context of the present application. The material is preferably made of a synthetic material; more preferably of a flexible synthetic material selected from the group consisting of polyester.

The thread can have a diameter in the range of from 0.19-0.25 mm.

In a preferred embodiment of the present invention, a monofilament polyethylene thread is used. This monofilament polyethylene thread preferably has a diameter of 0.225 mm.

In general, the arms of the carrier body can have any form suitable to prevent the accidental loss of the intrauterine contraceptive device when it is has been placed in the uterus, e.g. T- or V-form.

According to a preferred embodiment of the present inventions the arms are oriented to extend towards the oviducts.

The carrier body, the respective arms and the thread can be of any dimension suitable for the present invention. In general, the exact dimensions of the inventive intrauterine contraceptive device, such as the carrier body, its arms and the thread, are adapted to the size of the respective uterus.

The intrauterine contraceptive device according to the present invention can be inserted into the uterus with the help of any inserting tube and pushing sticks by any method know by a person skilled in the art.

FIG. 1 shows a possible embodiment of an intrauterine conceptive device according to the present invention. The carrier body 1 is equipped with arms 2 on the one side and an indicator thread 3 on the opposite side. The active metallic alloy 4 preferably is wounded in the form of a wire in a helical form onto a portion of the carrier body 1 located between the arms and the indicator thread.

The following table compares the efficacy of the $Zn_xCu_yMn_zAu_k$ (I)—and/or $Zn_xCu_yMn_zAg_k$ (II)—IUDs of the present invention with Cu-IUDs of the state of the art. The IUDs of the present invention provide an advantageous lower Pearl index, i.e. an increased contraceptive effectiveness associated with a shortened menstruation duration compared to the IUDs of the prior art.

| | Contraceptive effectiveness Pearl-index (36 months rates) | Duration of menstrual bleeding (day) |
|---|---|---|
| IUD of the present invention | <0.5 | 3-5 |
| Cu- IUD | 1-4.8 | 4-7 |

It is another object of the invention to use a metallic alloy of the formula $$Zn_xCu_yMn_zAu_k \quad \text{(I), or}$$

$$Zn_xCu_yMn_zAg_k \quad \text{(II),}$$

wherein x+y+z+k=100 weight %, x is in the range from approximately 18 to 30 weight %, z is in the range from approximately 0.5 to 3 weight %, k is in the range from approximately 3 to 12 weight %, and y being the balance, in an intrauterine device for performing a spermicide function on spermatozoa.

The invention claimed is:

1. An intrauterine contraceptive device comprising a carrier body and an active metallic alloy, characterized in that the active metallic alloy is of the formula $$Zn_xCu_yMn_zAu_k \quad \text{(I), or}$$

$$Zn_xCu_yMn_zAg_k \quad \text{(II),}$$

wherein
x+y+z+k=100 weight %,
x is in the range from approximately 18 to 30 weight %,
z is in the range from approximately 0.5 to 3 weight %,
k is in the range from approximately 3 to 12 weight %, and y being the balance.

2. The intrauterine contraceptive device of claim 1, wherein x+y is approximately 93 weight %.

3. The intrauterine contraceptive device of claim 1, wherein the carrier body is equipped with arms on one side and an indicator thread on the opposite side of the body.

4. The intrauterine contraceptive device of claim 1, wherein the carrier body is made of plastic.

5. The intrauterine contraceptive device of claim 4, wherein the plastic is polyethylene.

6. The intrauterine contraceptive device of claim 3, wherein the indicator thread is a monofilament polyester thread.

7. The intrauterine contraceptive device of claim 1, wherein the active metallic alloy is wire-shaped.

8. The intrauterine contraceptive device of claim 7, wherein the active metal alloy is placed onto the carrier body in a helical form.

9. A method of performing a spermicide function on spermatozoa which comprises using of a metallic alloy having the formula $$Zn_xCu_yMn_zAu_k \quad \text{(I), or}$$

$$Zn_xCu_yMn_zAg_k \quad \text{(II),}$$

wherein x+y+z+k=100 weight %, x is in the range from approximately 18 to 30 weight %, z is in the range from approximately 0.5 to 3 weight %, k is in the range from approximately 3 to 12 weight %, and y being the balance, in an intrauterine contraceptive device.

* * * * *